United States Patent

Yamazaki et al.

[11] Patent Number: 6,106,887
[45] Date of Patent: Aug. 22, 2000

[54] PROCESS FOR OBTAINING A MODIFIED CEREAL FLOUR

[75] Inventors: Katsutoshi Yamazaki; Takahiko Soeda, both of Kawasaki, Japan

[73] Assignee: Ajinomoto Co., Inc., Tokyo, Japan

[21] Appl. No.: 08/977,575

[22] Filed: Nov. 25, 1997

[30] Foreign Application Priority Data

Nov. 28, 1996 [JP] Japan ..................................... 8-317869

[51] Int. Cl.⁷ ...................................................... A21D 2/00
[52] U.S. Cl. ............................. 426/622; 426/20; 426/61; 426/549
[58] Field of Search ................................ 426/622, 20, 61, 426/62, 63, 64, 549, 94

[56] References Cited

U.S. PATENT DOCUMENTS

| | | |
|---|---|---|
| 5,055,310 | 10/1991 | Nonaka et al. . |
| 5,156,956 | 10/1992 | Motoki et al. . |
| 5,276,839 | 1/1994 | Gottmann et al. ........................ 426/61 |
| 5,518,742 | 5/1996 | Soeda et al. . |
| 5,658,605 | 8/1997 | Soeda et al. . |
| 5,681,597 | 10/1997 | Kuraishi et al. . |

FOREIGN PATENT DOCUMENTS

| | | |
|---|---|---|
| 0 492 406 A1 | 7/1992 | European Pat. Off. . |
| 5-15324 | 5/1993 | Japan . |

OTHER PUBLICATIONS

Watanabe et al., "Controlled enzymatic treatment of wheat proteins for production of hypoallergenic flour", 1994.

Patent Abstracts of Japan, vol. 15, No. 56 (C–0804), Feb. 8, 1991 & JP 02 286031 A (Showa Sangyo Co Ltd; Others: 01), Nov. 26, 1990, Abstract.

Patent Abstracts of Japan, vol. 96, No. 04, Apr. 30, 1996 & JP 07 327584 A (Ajinomoto Co Inc), Dec. 19, 1995, Abstract.

Database WPI, Section CH, Week 9618, Derwent Publications Ltd., London, GB; XP002081167 & JP 08 051944 A (Ajinomoto KK), Feb. 27, 1996, Abstract.

*Primary Examiner*—Lien Tran
*Attorney, Agent, or Firm*—Oblon, Spivak, McClelland, Maier & Neustadt, P.C.

[57] ABSTRACT

A method for modifying cereal flour by treating it with transglutaminase during the process of milling cereal flour, as well as processed foods containing the modified cereal-flour, such as noodles, breads, pastries.

5 Claims, No Drawings

PROCESS FOR OBTAINING A MODIFIED CEREAL FLOUR

BACKGROUND OF THE INVENTION

1. Field of the Invention

The present invention relates to a modified cereal flour and a cereal-flour processed food. The invention relates to a modified cereal flour produced by performing transglutaminase treatment during a process for producing cereal flour, such as wheat flour, from raw material cereal grains, and various cereal-flour processed foods including breads, pastas such as macaroni and spaghetti, Chinese noodles (including the wrappings of gyoza, wang-tang, and the like), Japanese noodles such as udon and soba, tempura, oil-fried quick breads such as doughnut, cakes, snacks, fresh pastries, and Japanese-style pastries.

2. Discussion of the Background

As to the modification of wheat flour for use in breads, pastries and cakes, a great deal of research has been carried out, conventionally. For example, 1. a method comprising putting wheat flour in the atmosphere of carbonate gas and ethanol at 40° C. or more (Japanese Patent Publication (Kokoku) No. 6-36725);

2. a method comprising adding water at 40 to 500 % by weight into the raw material wheat, drying the resulting wheat at a temperature that does not denature, to prepare the wheat as cereal flour for pastries (Japanese Patent Publication (Kokoku) No. 5-4055); and 3. a method comprising adding an oxidant and water into wheat flour, to recover gluten with excellent processability for processed food (Japanese Patent Publication (Kokoku) No. 6-34682).

Furthermore, reports have been published about a technique to modify wheat flour by using transglutaminase (hereinafter sometimes abbreviated as "TG"), which is an enzyme catalyzing the acyl transfer reaction of the γ-carboxyamide group in glutamine residues of peptides. For example, a method has been reported that comprises adding a given amount of TG to commercially available wheat flour for cakes, to prepare wheat flour with excellent taste and texture for cakes (Japanese Patent Laid-open (kokai) No. 2-286031). Also, a method involving adding TG to commercially available wheat flour to prepare dough with good elasticity for bread preparation (U.S. Pat. No. 5,279,839) has been reported.

All of the techniques described above are individually excellent from some standpoint. However, no technique which can overcome the majority of problems specific to wheat flour, as described below, has ever been reported. More specifically, the problems are:

1. deterioration, such as oxidation of wheat flour, occurs after long term storage;

2. wheat flour causes allergy;

3. preferable taste and texture often cannot be imparted to the final products (cereal-flour processed food) such as bread, pastries, cake, pasta and the like.

SUMMARY OF THE INVENTION

It is an object of the present invention to provide a cereal flour with unique properties, that is, wheat flour, with (1) no deterioration, such as oxidation, upon long term storage, and (2) with low allergy potential, and (3) capable of having the taste and texture preferred for final products, including bread, pastries, cake, pasta, etc.

The inventors have found that the major problems encountered with cereal flour can be overcome by transglutaminase treatment during production of a cereal flour, such as wheat flour, which is then used as a component of the cereal-flour processed product. More specifically, the present invention relates to a modified cereal flour obtained by performing transglutaminase treatment during: (1) the tempering process, and/or (2) the grinding process, for producing cereal flour from the raw material cereal grain and cereal-flour processed foods using such a modified cereal flour as the material.

As described above, examples of transglutaminase being used commercially to modify wheat flour are known. However, in those examples transglutaminase is used for treating raw materials, such as wheat flour milled from wheat. That is completely different from the present invention, in which transglutaminase is applied during the process of milling. The use of transglutaminase in the course of milling is more effective.

The aforementioned problems can he overcome, for example, by progressing the action of transglutaminase during a process of producing wheat flour. Additionally, the gel forming capacity, viscosity and water retention capacity of wheat protein contained in wheat flour can be improved, to readily provide a modified wheat flour highly ranked as a raw material of breads, tempura, cakes, fried quick breads such as doughnut and batter powder.

DETAILED DESCRIPTION OF THE INVENTION

The term "cereal flour" means any flour of wheat, barley, corn, Japanese soba-ko, rye, oats, Chinese millet, soy bean or a mixed flour of two or more of these cereal flours. These cereal flours are generally used for producing breads, pastas such as macaroni and spaghetti, Chinese noodles (including the wrappings of gyoza, wang-tang, and the like), Japanese noodles such as udon and soba, tempura, oil-fried quick breads such as doughnut, cakes, snacks, fresh pastries, and Japanese-style pastries.

The transglutaminase to be used for producing the modified cereal flour of the present invention is an enzyme catalyzing the acyl-transfer reaction of the γ-carboxyamide group in the glutamine residues in peptides. When the transglutaminase acts on the ε-amino group of the lysine residue in proteins as an acyl receptor, ε-(γ-Glu)Lys binding is formed intramolecularly or intermolecularly, whereby the cross-linking reaction of the protein in wheat flour as a main raw material for preparing the processed food is promoted, so that a wheat flour with properties such as higher gel formation capacity, a higher viscosity and higher water retention capacity can be obtained.

The detailed properties of the transglutaminase enzymes derived from microorganisms are described in Japanese Patent Laid-open (kokai) No. 64-27471.

Transglutaminase is divided into calcium-dependent and non-dependent types, and any of these types is satisfactorily used for producing the claimed modified cereal flour. Examples of the latter include those from microorganisms (see, for example, the Japanese Patent Laid open (Kokai) No. 64-27471 described above). Examples of the former include those from liver of guinea pig (see Japanese Patent Publication (Kokoku) No. 1-50382), those from animal blood (also referred to as "Factor XIII"), those from fish (see, for example, Journal of Japan Fisheries Academy, Vol. 56, page 125–132 (1990)) and Proceedings of Nippon Fishery Federation, 1994, page 219). Also, those produced by methods of genetic engineering can be included (see Japanese Patent Laid-open (Kokai) Nos. 1-300889 and 5-199883), and any of such transglutaminases can be used, satisfactorily, with no specific limitation on the origin and the preparation process.

In the case of production of wheat flour, the amount of transglutaminase to be added (to be used) in the process of preparing the modified cereal flour is 0.01 to 100 units (U), preferably 0.1 to 50 units (U) per 1 gram of the protein in the raw material wheat. If the amount of enzyme added is less than the range described above, the gel formation capacity is reduced. Also, in cases where the resulting modified cereal flour is used for the production of bread, the resulting bread turns too soft, and is not preferable; and if the amount is above the range, the resulting bread turns too hard, so that the taste and touch preferred for bread is deteriorated. Even if the type of raw material wheat is different, the concentration range of transglutaminase to be used is the same.

Commercially available enzyme formulations comprising transglutaminase as a main component may be used, for example, "Activa" (specific activity of 1 U/ml), manufactured by Ajinomoto Co., Inc.

In accordance with the present invention, the activity unit of the transglutaminase is assayed and defined as follows. After the reaction of transglutaminase with benzyloxycarbonyl-L-glutaminylglycine and hydroxyamine as substrates, to form an iron complex with the resulting hydroxamic acid in the presence of chloroacetic acid, the absorbence at 525 nm is measured. In such manner, a standard curve is prepared on the basis of the amount of hydroxamic acid, and the enzyme amount needed to generate 1 mol. hydroxamate per one minute is defined as 1 unit (U) of transglutaminase activity. As to the details of the assay, see the Japanese Patent Laid-open (Kokai) No. 64-27471.

When the transglutaminase treatment is carried out in the presence of a foreign protein and/or a partial protein hydrolysate, an effect of the present invention can be improved, such that the resulting wheat flour in a kneaded mixture with water has further increased elasticity and viscosity.

The term "foreign protein" means protein intentionally added extraneously for the transglutaminase treatment, excluding the protein naturally contained in cereal grain (cereals) to be milled. Such proteins include milk protein such as casein, sodium caseinate, calcium caseinate, whole fat dry milk, and skimmed dry milk; wheat protein; gelatin; collagen; corn protein such as zein; rice protein; soy bean protein such as separated soy bean protein, extracted soy bean protein and soy bean whey protein; egg protein such as egg white albumin; milk whey protein and the like.

Furthermore, the partial protein hydrolysates include partially hydrolyzed products of protein to be used as the foreign proteins, such as the partially hydrolyzed products of wheat protein, milk protein and so on.

The partial protein hydrolysates obtainable by partially hydrolyzing wheat protein and milk protein, using enzymes, acids and alkalis according to routine methods, can be used. No specific limitation is imposed as long as the partial protein hydrolysate can achieve the objects of the present invention.

Furthermore, commercially available peptides such as lysine peptide and glutamine peptide may be used as the partial protein hydrolysate and have the same effects as the partial protein hydrolysates derived from natural proteins, as described above. Therefore, the partial protein hydrolysate in accordance with the present invention includes peptides such as lysine, the single amino acid.

The average molecular weight of the partial protein hydrolysate to be used in accordance with the present invention is generally about 600 to 40,000 Daltons, preferably about 3,000 to 20,000 Da and more preferably about 6,000 to 16,000 Da.

The amount of foreign protein and/or partial protein hydrolysate to be added (to be used) is 0.001 to 2.0 g, preferably 0.01 to 1.0 g per 1 gram of the protein of wheat, when the raw material cereal grain is wheat. The amount thereof to be added does not vary even if the foreign protein or the partial protein hydrolysate are used singly or in combination of both the foreign protein and the partial protein hydrolysate. That is, the total amount of the two is fixed in the above-mentioned range. If the amount thereof to be added is less than 0.001 g, the noodles produced from the resulting wheat flour cannot get improved limpness and elasticity; or the wrappings of gyoza, wang-tang, and the like cannot be improved. When the amount is above 2.0 g, noodles and the wrappings of gyoza, wang-tang, and the like are disadvantageously fragile, with a non-viscous texture. In any case, the initial objects of the invention cannot be attained.

A method for producing the modified cereal flour of the present invention from cereal grain, by concurrently using the transglutaminase described above, and, if desired, a foreign protein and/or a partial protein hydrolysate, is now described in detail below.

First, the concept of milling is described for the sake of deep understanding. As is well known of milling: "Cereals with the outer side composed of soft sugar layers and with the inner endosperm being hard, like rice grains, are shaved from the outside to separate the edible part, i.e., rice pearling. On the other hand, cereals with the outer sheath being very strong but with the endosperm being fragile and readily broken and, additionally, with longitudinal grooves at the grain center, should be pulverized to separate the sheath part, i.e, milling. To effectively utilize gluten specific to wheat, wheat is necessarily prepared as wheat flour. The milling process is summarized as follows.

1. Selection—A process of removing micro-fine contamination such as stone. Because it is difficult to remove impurities from the resulting wheat flour, selection of raw material wheat should be done very carefully.

2. Tempering and blending—For strengthening the sheath, separating the endosperm part easily, and softening the endosperm part for ready milling, water is added to wheat, which is then rested for 24 to 48 hours, for tempering. Additionally, wheat raw materials separately tempered are blended together, if necessary, depending on the object.

3. Grinding—The sheath of the tempered wheat is separated as much as possible by means of a brake roll, to recover crude grain of the endosperm (disruption process). Then, sifting the crude grain and transferring the grain to a purifier, to remove the contaminated debris of the sheath by a combination of sifting and draft selection (purification process). Furthermore, the purified crude grain is ground by means of a smooth roll (smooth face or crude face), followed by separating the flour by grain size through sifting (pulverization process).

4. Blending of wheat flour—After sifting, wheat flours of various sizes (finished flour; agariko in Japanese) are blended together, depending on the properties thereof, so as to prepare a wheat flour of the objective quality and grade.

5. Finishing—A final product is produced after thorough mixing. Vitamins and the like should be mixed into the product as a dietary supplement, (see "General Dictionary of Food Industry", new edition, issued by Korin K.K, 1993). Such milling techniques are applicable to other cereal grains (cereals) having a similar structure as that of wheat.

The claimed transglutaminase treatment during milling will now be described by referring to the example of wheat. Other steps in the production of the present modified wheat flour are carried out according to well-known methods starting from raw material wheat.

The preferred protein content of a wheat flour varies depending on its use. Additionally, the protein content of wheat flour varies depending on the type of raw material wheat. Wheat flour is divided into gluten-rich wheat flour (grade I; kyoriki-ko in Japanese), semi-gluten-rich wheat flour (grade II; jun-kyoriki-ko in Japanese), moderately-gluten-rich wheat flour (grade III; churiki-ko in Japanese), gluten-poor wheat flour (grade IV; hakuriki-ko), durum semolina flour, and the like. In accordance with the present invention, any of these wheat flours can be modified effectively.

The transglutaminase treatment in the course of the tempering process can be performed for example as follows.

Using Canada Western Red Spring wheat as a semi-gluten-rich wheat flour (grade II), transaminase is added during the course of water addition during the tempering process in the amount of 0.01 to 100 U, preferably 0.1 to 50 U per 1 gram of protein in the raw material wheat, together with a foreign protein and/or a partial protein hydrolysate, if desired, in an amount of 0.001 to 2.0 g, preferably 0.01 to 1.0 g total per 1 gram of protein in the wheat. The amount of water added is not specifically limited, but generally, water is added so that the final water content in the wheat is about 10 to 20%, preferably about 12 to 16%. Subsequently, tempering is effected generally at 0 to 60° C., preferably at 10 to 30° C., for 16 to 50 hours, so that transglutaminase is permeated from the surface of the wheat grain through the germ part to the inside, to promote the crosslinking of gluten in the wheat protein. Through such tempering, the endosperm is readily pulverized, while the epidermis absorbs water moderately and also gets hard, due to the action of transglutaminase, so that the resulting grain turns so fragile as to be readily disrupted. Additionally, the gluten in the protein inside the endosperm is crosslinked, so that a wheat flour with elasticity and capable of imparting suppleness to the resulting noodles can be recovered. The wheat flour obtained by such transglutaminase treatment is a modified wheat flour with improved performance of the present invention.

A transglutaminase treatment conducted during the grinding process is carried out for example as follows.

To the raw material wheat after tempering and blending is added water 1 to 3 hours prior to the grinding process. Transglutaminase, and, if desired, a foreign protein and/or a partial protein hydrolysate, have been dissolved or dispersed in the water. The wheat is subjected to a procedure to separate the endosperm from the epidermis (disruption process), and thereafter, routine milling procedures are effected to recover the modified wheat flour of the present invention. The amount of transglutaminase to be then added is 0.01 to 100 U, preferably 0.1 to 50 U, per 1 g of the protein of the raw material wheat; and the amount of the foreign protein and/or the partial protein hydrolysate to be added in total is 0.001 to 2.0 g, preferably 0.01 to 1.0 per 1 g of the protein of the raw material wheat.

The transglutaminase treatment is carried out at either the tempering process or the grinding process as described above, but in some cases, the treatment may be carried out during both the tempering process and the grinding process.

Furthermore, the transglutaminase treatment can be effected at a process subsequent to the grinding process, but the effect is not as good. For example, transglutaminase treatment of the wheat flour (finished flour) at the blending or finishing process, after the grinding process, is effected for example as follows.

Transglutaminase in the amount of 0.01 to 100 U, preferably at 0.1 to 50 U per 1 g of protein in the wheat flour is preliminarily dissolved in an appropriate amount of water. If desired, a foreign protein and/or a partial protein hydrolysate is added after the grinding process, at 0.001 to 2.0 g, preferably 0.01 to 1.0 g per 1 g of the wheat protein, together with transglutaminase, followed by dissolution or dispersion. Subsequently, the resulting solution is sprayed over the wheat flour through the pulverization process (last process of the grinding process), to be aged at 5 to 35 ° C. for 15 minutes to 48 hours, preferably 1 to 24 hours. During the "aging" process, the transglutaminase exerts its action. The wheat flour through the "aging" process is dried in air and finished as a product.

The present methods for modifying wheat flour are significantly different from prior art using transglutaminase, such as those described by the Japanese Patent Laid-open (Kokai) No. 2-286031 and U.S. Pat. No. 5,279,839, in that transglutaminase should exert its action as part of a milling process to produce wheat flour from raw material wheat, i.e, an agricultural product.

Description of a cereal-flour processed food using the modified cereal flour of the present invention follows. Processed food containing the modified cereal flour of the present invention can be made by conventional methods for producing cereal-flour processed food, except for using the claimed modified cereal flour as the raw material cereal flour.

Bread can be produced as follows. Yeast, yeast food and water are kneaded into the raw material modified wheat flour of the present invention by means of a mixer. Subsequently, the kneaded mixture is kept at 20 to 40 ° C. for from 20 minutes to 10 hours to effect a first fermentation, to prepare an intermediate seed dough. Water, edible salt, sugars, oil, skimmed dry milk and the like are added to and kneaded with the intermediate seed dough, to prepare a bread dough. The bread dough is divided appropriately into portions, which are left to stand at 20 to 40° C. for a given time for the purpose of forming the network structure of wheat gluten (fermentation) and are then filled in a baking pan. Subsequently, fermentation is again progressed. The total fermentation time is about 20 minutes to 12 hours. After completion of fermentation, the dough is baked in an over at 180 to 250° C.

The loaf of bread obtained by baking is excellent in that the bread can maintain good taste and properties, for example, the capacity to maintain the final shape of the bread even after long-term storage.

It is needless to say that the direct kneading process comprising kneading together all of the modified wheat flour, yeast and other raw materials prior to the first fermentation is satisfactory to prepare a loaf of bread, besides the intermediate seed dough preparation method. The first fermentation is carried out by keeping the kneaded product at a temperature of 20 to 45° C. for 30 minutes to 10 hours. A subsequent fermentation process is done under general fermentation conditions for preparing bread. The fermentation conditions have no specific limitations. If necessary, the bread dough may be again fermented, after resting at a temperature of 20 to 45° C.

Furthermore, instead of baking, steamed bread can be recovered by heating dough in steam. Heating in steam is done according to general methods.

Other ingredients routinely used for preparing bread include skimmed dry milk, eggs, polysaccharides, fruit, coffee extract components, spices, seasonings, additives such as ascorbic acid, swelling agents (ammonium hydrogen carbonate, sodium hydrogen carbonate etc.), bleaches (ammonium persulfuric acid, potassium bromate, etc.), quality modifiers (calcium stearoyllactate, L-cysteine hydrochloride, etc.), emulsifiers (glycerin fatty acid ester, sucrose fatty acid ester, etc.), in addition to the raw material modified cereal wheat flour, yeast, yeast food, water, edible salt, sugar and fat.

Fried quick breads, such as doughnuts, using the the modified cereal flour of the present invention as the principal component are prepared according to routine methods. Secondary raw materials are not specifically limited, and, therefore, sugar, eggs, egg white, cream, butter, milk, seasoning, edible salt, spices and the like are used if necessary. Fried quickbread, such as doughnuts, made with the modified wheat flour of the present invention are very tasty.

Cakes, such as sponge cake, are made with the modified cereal flour of the present invention using routine methods. Secondary raw materials have no specific limitation, and therefore, eggs, sugar, milk, butter and the like, being usually used, are appropriate. The sponge cake can be prepared using general equipment.

For example, foamed meringue is prepared by adding sugar into egg yolk, using a Hobart mixer at a low speed for good agitation, and simultaneously adding egg white and sugar into the resulting mixture.

Subsequently, the modified wheat flour of the present invention is added to and mixed with the meringue, followed by addition of melted butter if necessary and further gradual agitation at a low speed for mixing them together. The dough is poured into a pan, followed by baking on medium flame at 160 to 180° C. for about 30 minutes, thereby preparing sponge cake. The sponge cake obtained by using the modified wheat flour of the present invention provide good taste with the desired elasticity.

Japanese style pastries prepared using the modified cereal flour of the present invention may follow general methods. In the case where the Japanese-style pastry is a type of bean pastry covered with a cherry blossom leaf (sakura-mochi), water is added, together with sugar and rice flour as secondary raw materials, into the modified wheat flour, followed by mixing and kneading to prepare a dough. Then, boiled, mashed, strained azuki bean in jam (koshi-an in Japanese) is covered with a wrapping prepared from the dough, and the resulting stuffed matter is further rolled with a salted cherry blossom leaf, to prepare a sakura-mochi. The sakura-mochi using as the principal raw material the modified wheat flour can keep softness even after a long time passes and is tasty.

Pastas, such as spaghetti and macaroni, Japanese noodles such as udon and soba, and Chinese noodles (including the wrappings of gyoza, wang-tang, and the like) may satisfactorily follow routine methods, except that the modified cereal flour of the present invention should be used, in place of conventional cereal flour.

For pasta, for example, water is added to and kneaded with the modified wheat flour and whole egg powder for routine use as a secondary raw material, to prepare pasta dough. The dough is then rested at a given temperature (the so-called "aging" process), followed by primary rolling, lumping and press rolling, and the resulting dough is finally cut into the desired width and length to prepare pasta strips. The pasta strips are boiled in water, together with a small amount of edible salt, and the resulting pasta can get preferable hardness, excellent crispness and preferable elasticity. This could possibly be due to the formation of a network structure in the gluten of wheat owing to the action of transglutaminase.

It is needless to say that the modified wheat flour of the present invention can be used for producing noodles other than pasta, such as Japanese noodles including udon and soba, Chinese noodles and the like. The overall production of these noodles can be done according to methods conventionally used, except for the use of the modified cereal f flour, instead of conventional cereal flour.

EXAMPLES

Example 1 (Chinese noodles)

A modified wheat flour from a raw material Canadian wheat (Canada Western Red Spring species; 9 kg) was prepared as follows.

Firstly, micro-fine stone, micro-fine iron debris and the like were removed from the raw material wheat (selection process). The selected wheat was placed in a tank to which was added water to the extent that the final water content in the wheat was about 14.7 %. The wheat was kept as it was at 25 ° C. for 24 hours (tempering process). Transglutaminase was previously added to and dissolved in the water to be added, to a final concentration of 5 U per 1 g of the wheat protein.

After tempering, the wheat sheath was separated to recover crude grain of the endosperm (disruption process). Then, contaminated sheath debris was removed from the crude grain of the endosperm by means of a combination of sifting and draft selection (purification process). Furthermore, the purified crude grain was ground with a smooth roll and sifted by the size of the grain (pulverization process), to obtain 7 fractions, depending on the size.

Among the 7 fractions thus recovered, wheat flour of a second largest size and wheat flour of a fourth largest size were blended together (blending process), followed by sufficient mixing (finish process). The modified wheat flour thus obtained was defined as Inventive Product 1.

A modified wheat flour obtained by the same milling process, except for the addition of 10 U of transglutaminase instead of 5 U per 1 gram of the wheat protein at the tempering process, was defined as Inventive Product 2. Similarly, a modified wheat flour obtained by a milling process including transglutaminase treatment with addition of 5 U of transglutaminase per 1 gram of the wheat protein and addition of 0.1 g of the partial protein hydrolysate of wheat protein per 1 g of the wheat protein was defined as Inventive Product 3; and a modified wheat flour obtained by a milling process including transglutaminase treatment with addition of 5 U of transglutaminase per 1 g of the wheat protein and addition of 1.0 g of the partial protein hydrolysate of wheat protein per 1 g of wheat protein was defined as Inventive Product 4. In the latter case, the partially hydrolyzed product of wheat protein had an average molecular weight of about 7,000 Da (trade name; Glutamine peptide, manufactured by "Canpina Milk Uni-Japan").

As a control product, wheat flour produced without a transglutaminase or a partial protein hydrolysate, namely general wheat flour, was used.

TABLE 1

| Wheat flour | Transglutaminase | Glutamine peptide g/g wheat protein |
|---|---|---|
| Control product | 0 | 0 |
| Inventive Product 1 | 5 | 0 |
| Inventive Product 2 | 10 | 0 |
| Inventive Product 3 | 5 | 0.1 |
| Inventive Product 4 | 5 | 1.0 |

The four types of modified wheat flours and the control sample were individually weighed at 2000 g, and blended edible salt (20 g), Chinese noodle seasoning (Kansai; 20 g) and water (800 g) were added followed by kneading at 500 mmHg by means of a vacuum mixer (vacuum mixer of type TVM 03-0028, manufactured by Tokyo Noodle Machine, Co.) for 10 minutes. Subsequently, the resulting kneaded product was rolled loosely by means of a noodle machine manufactured by Shinagawa Noodle Machine, K.K., followed by lumping twice and press rolling four times and the resulting product was cut out, to prepare five types of Chinese noodles.

A sensory evaluation of the Chinese noodle samples by a panel of 10 experts was carried out by a 10-point scoring method, under the provision that the control product be scored as 5 points. The average points are shown in Table 2. Additionally, cutting energy was measured by a cutting test method with a rheometer, and the results are shown in the same table. In the table, furthermore, the representation of individual Chinese noodle types respectively corresponds to the representation of the wheat flours as the raw materials. For example, the Chinese noodle of the Inventive Product 2 is prepared from the modified cereal flour of the Inventive Product 2.

TABLE 2

|  | Sensory Evaluation | | | Property cutting energy (erg/cm$^2$) |
|---|---|---|---|---|
|  | elasticity | viscosity | limpness |  |
| Control Product | 5 points | 5 points | 5 points | 11.2 × 10$^4$ |
| Inventive Product 1 | 7.0 | 7.0 | 7.1 | 17.2 × 10$^4$ |
| Inventive Product 2 | 6.9 | 7.6 | 7.7 | 17.8 × 10$^4$ |
| Inventive Product 3 | 8.5 | 8.6 | 8.4 | 18.6 × 10$^4$ |
| Inventive Product 4 | 9.1 | 9.2 | 9.0 | 19.3 × 10$^4$ |

Table 2 indicates that Chinese noodles prepared from all of the modified wheat flours treated by the transglutaminase alone, as well as treated by a combination of transglutaminase and a partial protein hydrolysate, are excellent from the sensory respect and also have greater cutting energy, an objective parameter. The data show that Chinese noodles obtained by using the present modified wheat flours have the most suitable taste as noodles.

Example 2 (A loaf of bread)

Four types of modified wheat flours and a control product were made in the same manner as in Example 1, except for the use of a partial protein hydrolysate of wheat protein having an average molecular weight of about 10,000 (trade name; MA-Z, manufactured by Morinaga Milk Industry, Co., Ltd.) instead of having an average molecular weight of about 7,000 (trade name; Glutamine peptide, manufactured by Canpina Milk Uni-japan).

1400 g each of the four types of modified wheat flours and the control product, were weighed, followed by addition of yeast (40 g), yeast food (2.5 g) and water (750 g) and subsequent mixing at a low speed for 2 minutes, next at medium speed for 4 minutes and then at high speed for 1 minute with a Hobart mixer. After that, processed fat (50 g) was added to the resulting dough, followed by another mixing at an intermediate speed for 3 minutes and high speed for 1 minute. Then, the dough was kept under the condition of 27° C. and 75% RH (Relative Humidity) for 4 hours, as first fermentation to obtain intermediate seed dough. The dough on completion of fermentation was at 28° C. and pH 5.3. To the intermediate seed dough were added other ingredients (40 g of edible salt, 60 g of sugar, 60 g of glucose, 60 g of shortening, 40 g of skimmed dry milk and 440 g of water), followed by kneading with a mixer to prepare bread dough. The bread dough was kept at the above-mentioned temperature for about 10 minutes (second fermentation), which was then divided equally in 6 portions and further kept at 28° C. for 10 minutes (third fermentation). Then, the resulting dough was filled in a pan. The dough was kept under conditions of 37° C. and 75% RH for 50 minutes for another fermentation (fourth fermentation). Subsequently, the fermented bread dough was placed in an oven, for baking at 220° C. for 40 minutes to prepare five types of loaves of bread.

According to the following method, the resulting five types of loaves of bread were evaluated in an organoleptic manner. More specifically, the loaves of bread 4 days after baking were sliced at a 1.5-cm thickness, and then they were evaluated by a panel of 10 specialists. Additionally, evaluation was carried out by the 10-point method on the basis of the scoring shown in Table 3 below, wherein individual items of the control product were scored as 5 points. The average point of each result of five evaluation items, i.e. surface color, surface quality, acid expansion, inner color phase and texture, is shown in Table 4 below.

TABLE 3

| Evaluation Standard | 10 very strong |
|---|---|
|  | 9 fairly strong |
|  | 8 strong |
|  | 7 relatively strong |
|  | 6 slightly strong |
|  | 5 normal |
|  | 4 slightly weak |
|  | 3 relatively weak |
|  | 2 weak |
|  | 1 fairly weak |
|  | 0 very weak |

TABLE 4

|  | Surface color | Surface quality | Crumb grain | Inner color phase | Texture |
|---|---|---|---|---|---|
| Control Product | 5 points | 5 points | 5 points | 5 points | 5 points |
| Inventive Product 1 | 8.0 | 7.0 | 7.5 | 8.0 | 7.5 |
| Inventive Product 2 | 8.5 | 7.5 | 7.5 | 8.5 | 7.5 |
| Inventive Product 3 | 8.5 | 8.5 | 8.0 | 8.5 | 7.5 |

TABLE 4-continued

|  | Surface color | Surface quality | Crumb grain | Inner color phase | Texture |
|---|---|---|---|---|---|
| Inventive Product 4 | 9.0 | 9.0 | 8.5 | 8.5 | 7.6 |

Table 4 indicates that all the loaves of bread (Inventive Products) prepared by using the modified wheat flours treated by only transglutaminase or a combination of transglutaminase and a partial protein hydrolysate were excellent from a sensory standpoint compared with the control product.

Example 3 (Sponge cake)

A modified wheat flour was prepared by using American wheat (Standard White species; 10 kg) as the raw material. Firstly, micro-fine stones and the like were removed from the raw material wheat (selection process). Then, the wheat was placed in a tank, followed by addition of water to the extent that the final water content in the wheat was about 14.3%. The resulting wheat was kept as it was, at 25° C. for 36 hours (tempering process). Then, transglutaminase was added to and dissolved in water to be added, at a rate of 1 U per 1 g of wheat protein. After tempering, the wheat sheath was separated, to obtain crude grain of the endosperm (disruption process). Then, contaminated sheath debris was removed from the crude grain of the endosperm by means of a combination of sifting and draft selection (purification process). Furthermore, the purified crude grain was ground with a smooth roll (pulverization process). Subsequently, the resulting flour was sifted, depending on the size of the flour, to obtain 7 fractions, depending on the size.

Among the 7 fractions thus recovered, a wheat flour of a second largest size and a wheat flour of a fourth largest size were blended together (blending process), followed by sufficient mixing (finish process). The modified wheat flour thus obtained was defined as Inventive Product 1.

By the same milling process, except for the use of 1 U of transglutaminase per 1 g of the wheat protein and 0.1 g of sodium caseinate (manufactured by Nissei Kyoeki, Kabushiki Kaisha) per 1 g of the protein in wheat, Inventive Product 2 was recovered.

TABLE 5

|  | Amount of transglutaminase (U/g) protein | Amount of sodium caseinate (g/g wheat flour) |
|---|---|---|
| Control Product | 0 | 0 |
| Inventive Product 1 | 1 | 0 |
| Inventive Product 2 | 1 | 0.1 |

By using the two types of modified wheat flours and control wheat flour (wheat flour obtained in the same manner except that the transglutaminase treatment was not done), sponge cake of the composition in Table 6 was prepared by routine methods.

TABLE 6

| Composition of sponge cake | |
|---|---|
| Raw material | Composition |
| Modified wheat flour or Control wheat flour | 200 g |
| Sugar | 200 g |
| Whole egg | 180 g |
| Water | 85 ml |

More specifically, whole egg was placed in a bowl, followed by addition of water (45 ml) and thorough mixing with a Hobart mixer, and to the resulting mixture was added sugar. Then, the mixture was adjusted to 300° C. Subsequently, the mixture was foamed at a high speed for 8 to 10 minutes. After adding the remaining water (40 ml) to the mixture, the mixture was foamed for 2-min at a high speed and subsequently for 1-min at a low speed, thereby cake dough was prepared. The modified wheat flours or the control wheat flour was added to the cake dough, followed by sufficient mixing. The resulting dough was placed in a pan, followed by smoothing the surface by means of a plastic pallet, and the resulting dough was then baked in an over at 180° C. for 30 minutes. After baking, the product was drawn out from the pan and cooled to room temperature, which was then subjected to sensory evaluation by a panel of 10 experts. The evaluation results are shown in Table 7. Furthermore, the appearance and inner phase were observed; and the volume of the cake was measured. These results are also shown in the same table. The overall evaluation based on all of these results is also shown in the same table. The symbols X, Δ, ○ and ◉ (double circle) represent not good, normal, relatively good and very good, respectively.

|  | Appearance | Cake volume | Inner phase | Texture | Overall |
|---|---|---|---|---|---|
| Control Product | recess at center | 2400 ml | pale yellow | slightly hard | X |
| Inventive Product 1 | no recess | 2450 | white | soft and smooth | ◉ |
| Inventive Product 2 | no recess | 2480 | white | soft and smooth | ◉ |

As shown in the above table, sponge cakes (the inventive products) with a larger volume without recess at the center and preferably with soft and smooth texture, were prepared, compared with the control product.

Example 4

Four type of modified wheat flours were prepared using the same procedures as in Example 1, and a control product. The extensograms of the four types of the modified wheat flours and the control wheat flour were measured by the following method. The secondary processing properties of wheat flour are measured by extensogram.

Subsequently, 300 g each of the four types of modified wheat flours and the control wheat flour were placed in a farinogram mixer (trade name; "Farinogram", manufactured by Brabender, Co.), followed by addition of 6 g of edible salt and an appropriate amount of pure water, to prepare dough. More specifically, the amount of pure water was adjusted so that a peak of the curve of the dough after 1-min kneading, 5-min holding and another 2-min kneading might be 500 B.U., to prepare dough.

From the dough thus prepared, 150 g thereof was drawn out and molded in a molding machine, which was then kept in a thermostat at 30° C. for 45 minutes. After that a first measurement of the extensogram was done. Forty-five minutes after another molding (namely 90 minutes after the initiation of first keeping), a second measurement was done. Forty-five minutes after further molding (namely, 135 minutes after the initiation), a third measurement was done. Herein, the measurement was carried out with a machine called "Extensograph" manufactured by Barbender, Co. The data 135 minutes later is shown in Table 8, which functions as the optimum indicator of the elasticity of wheat. Herein, the secondary processing functions as the optimum indicator of the elasticity of wheat. Herein, R in the table represents tensile resistance, which is the peak height of the curve of an extensogram measured (the unit is B.U.) Additionally, E represents extension, which is the length of the curve of the measured extensogram (the unit is mm). Furthermore, R/E represents shape coefficient, which is a value of tensile resistance divided by extension. A larger R/E represents a higher elasticity of wheat flour.

TABLE 8

|  | Control Product | Inventive Product 1 | Inventive Product 2 | Inventive Product 3 | Inventive Product 4 |
|---|---|---|---|---|---|
| Tensile resistance (R) | 278 | 415 | 570 | 525 | 585 |
| Extension (E) | 218 | 157 | 180 | 121 | 110 |
| Shape Coefficient (R/E) | 1.28 | 2.64 | 3.17 | 4.34 | 5.32 |

As shown in Table 8, all the Inventive Products were wheat flours having higher elasticity than that of the control product.

According to the present invention, modified cereal flour with excellent processability can be readily produced, and thus, cereal-flour processed food of high quality can be readily produced. In accordance with the present invention, furthermore, transglutaminase is added to function during a process of producing wheat flour from wheat as an agricultural product, to give a wheat flour having excellent processability. Therefore, flour industries can readily manufacture and sell wheat flour of high quality The advantages of the present invention for the flour industries are enormous.

The modified wheat flour of the present invention has lower allergen properties and hardly deteriorates under long term storage compared with conventional products. Specifically, transglutaminase treatment in combination with a foreign protein and/or a partial protein hydrolysate causes far less allergy.

Numerous modifications of the present method are apparent to those skilled in the art. In light of the above teachings the invention may be practiced otherwise than as specifically recited below.

The disclosure of Japanese priority application 317869/1996 filed Nov. 28, 1996, is hereby incorporated by reference.

We claim:

1. A method for modifying a cereal flour comprising:

tempering a raw material wheat with water containing 0.01 to 100 units of transglutaminase per gram of protein in the wheat, wherein said tempering is performed by adding water so that the final water content in the wheat is about 10 to 20%, and grinding to obtain flour.

2. The method of claim 1, wherein the tempering treatment is carried out in the presence of a foreign protein or a partial protein hydrolysate.

3. The method of claim 1, wherein the tempering treatment is carried out by using 0.1 to 50 units of transglutaminase per gram of protein in the cereal grain.

4. The method of claim 3, where said foreign protein is wheat protein or milk protein, and said partial protein hydrolysate is of wheat protein or milk protein.

5. The method of claim 1, wherein said raw material wheat is Canada Western Red Spring wheat.

* * * * *